(12) United States Patent
Bernhard et al.

(10) Patent No.: US 6,555,391 B1
(45) Date of Patent: Apr. 29, 2003

(54) METHODS OF CONDITIONING AN AFFINITY RESIN AFTER STORAGE

(75) Inventors: Susan L. Bernhard, Menlo Park, CA (US); Robert Toso, Danville, CA (US); Van Taiariol, Redwood City, CA (US)

(73) Assignee: Baxter International, Inc., Deerfield, IL (US)

( * ) Notice: Subject to any disclaimer, the term of this patent is extended or adjusted under 35 U.S.C. 154(b) by 0 days.

(21) Appl. No.: 09/639,179

(22) Filed: Aug. 15, 2000

(51) Int. Cl.$^7$ ............... G01N 33/53; G01N 33/543; G01N 33/44; G01N 30/02

(52) U.S. Cl. ............... 436/518; 436/8; 436/85; 436/161; 436/174; 436/176; 436/178; 436/518; 436/523; 436/524; 436/528; 436/529; 436/530; 436/531; 436/532; 436/533; 436/541; 436/823; 436/824; 435/4; 435/6; 435/7.1; 435/7.9; 435/174; 435/176; 435/177; 435/178; 435/179; 435/180; 435/181; 435/183; 435/803; 435/814; 435/963; 422/40

(58) Field of Search ............... 435/4, 6, 7.1, 7.9, 435/7.92, 174, 176–181, 183, 803, 814, 963; 436/518, 524, 8, 85, 161, 523, 528–533, 541, 174, 176, 178, 823, 824

(56) References Cited

U.S. PATENT DOCUMENTS 5,126,412 A * 6/1992 Das et al. ............ 525/504
5,525,472 A * 6/1996 Lifshitz et al. ............ 435/69.6
6,150,151 A * 11/2000 Khandke ............ 435/200

OTHER PUBLICATIONS

Tharakan et al. Physical and biochemical characterization of five commercial resins for immunoaffinity purification of Factor IX. Journal of Chromatography. (1992) vol. 595, Nos. 1–2, pp. 103–111.*

Highsmith et al. Evaluation of cyanogen bromide, FMP and hydrazide resins for immunoaffinity purification of Factor IX. Biotechniques. (1992) vol. 12, No. 3, pp. 418, 420, 422–423.*

Harlow and Lane: "Antibodies—A Laboratory Manual" *Cold Springs Harbor Laboratory Publications, N.Y.* (1988).

Ubrich and Rivat: "Antibodies Released From Immunoadsorbents: Effect of Support, Activation and Elution Conditions" *Art, Cells, Blood Subs., and Immob. Biotech.* 24:65–75 (1996).

Antonsen et al.: "Elution Conditions and Degradation Mechanisms in Long–Term Immunoadsorbent Use" *Biotechnol. Prog.* 7:159–172 (1991).

van Sommeren et al.: "Comparison of three activated agaroses for use in affinity chromatography: effects on coupling performance and ligand leakage" *J. Chromatrography* 639:23–31 (1993).

Scopes, R.K.: "Protein Purification, Principles and Practice" pp. 111–135, *Springer–Verlag New York Inc.* (1982).

Kohn and Wilchek: "The Use of Cyanogen Bromide and other Novel Cyanylating Agents for the Activation of Polysaccharide Resins" *Applied Biochem. and Biotechnol.* 9:285–305 (1984).

March et al.: "A Simplifed Method for Cyanogen Bromide Activation of Agarose for Affinity Chromatography" *Anal. Biochem.* 60:149–152 (1974).

Jennissen, H.P.: "Cyanogen Bromide and Tresyl Chloride Chemistry Revisted: The Special Reactivity of Agarose as a Chromatographic and Biomaterial Support for Immobilizing Novel Chemical Groups" *J. Mol. Recog.* 8:116–124 (1995).

Desai, M.A.: "Immunoaffinity Adsorption: Process–Scale Isolation of Therapeutic–Grade Biochemicals" *J. Chem. Techn. Biotechnol.* 48:105–126 (1990).

Berry and Pierce: "Stability of immunoadsorbents comprising antibody fragments. Comparison of Fv fragments and single–chain Fv fragments" *J. Chromatog.* 629:161–168 (1993).

Wilchek et al.: "Structure of a Soluble Super–Active Insulin Is Revealed by the Nature of the Complex Between Cyanogen–Bromide–Activated Sepharose and Amines" *Proc. Nat. Sci. USA* 72:1055–1058 (1975).

* cited by examiner

Primary Examiner—Long V. Le
Assistant Examiner—Kartic Padmanabhan
(74) Attorney, Agent, or Firm—Townsend and Townsend and Crew LLP (57) ABSTRACT

This invention relates methods for conditioning affinity chromatography resins to decrease leaching of the ligand during purification. The methods involve incubating the resin in a buffered solution of a hydroxyalkylamine compound (e.g., ethanolamine) prior to use of the resin for an affinity purification. The treatment removes unstably bound ligand from the resin.

20 Claims, 8 Drawing Sheets

METHODS OF CONDITIONING AN AFFINITY RESIN AFTER STORAGE

CROSS-REFERENCES TO RELATED APPLICATIONS

Not applicable.

BACKGROUND OF THE INVENTION

Affinity chromatography is a powerful method used to purify molecules and pharmaceutical compounds. A wide variety of molecules have been purified using various affinity purification schemes. Generally, the synthesis of affinity chromatography supports involves coupling a ligand having an affinity for the molecule being purified to a chromatography support. Through the specific interactions between the molecule and its ligand, significant increases in the purity of the molecule over the starting material can be achieved or significant amounts of a molecule can be removed from a starting material.

Typically, the synthesis of affinity chromatography resins involves reacting a ligand with a functional group on a chromatographic support or a derivatized group on a chromatographic support to form a ligand-matrix bond. Unfortunately, not all ligand-chromatographic support bonds are stable and the chromatographic support itself may trap ligands (or complexes of ligands) that are not bound to a functional group. Furthermore, these ligands can leach from the column during purification, contaminating the product. This is often a serious concern, especially in the pharmaceutical arena. Often regulatory agencies will issue strict guidelines to pharmaceutical companies for the amount of ligand that can be present in a pharmaceutical composition; during the regulatory approval process and on approved drugs, regulatory agencies (e.g., the FDA in the US) require that stringent limits (or specifications) be met on the amounts of contaminants such as ligands that can be present in the pharmaceutical. Thus, the presence of these contaminants can result in a ruined batch of the pharmaceutical or in increased expenditures of time and effort to further purify the pharmaceutical away from the ligand. Moreover, immunization of patients against the drug or anaphylactic shock could result if the ligand contaminant is an antibody and the molecule is used in a clinical setting (Ubrich and Rivat (1996) *Art. Cells, Blood Subs., and Immob. Biotech.* 24: 65–75). Therefore a need in the art exists for methods of decreasing the amount of ligand that leaches from an affinity column during purification of the molecule of choice. The present invention fulfills these and other needs.

SUMMARY OF THE INVENTION

The present invention provides methods for conditioning a chromatography resin after storage. The methods involve contacting a chromatography resin with an effective amount of a hydroxyalkyl amine compound that comprises at least one hydroxyl moiety. An example of a suitable compound is ethanolamine. The methods are generally used on a chromatography resin that is composed of a ligand that was conjugated to a chromatographic support at least 48 hours prior to contacting the chromatography resin with the hydroxyalkyl amine compound. For example, the invention provides methods for conditioning a chromatography resin that consists of an activated hydroxyl chromatographic support to which is attached an affinity ligand.

The invention also encompasses methods for preparing an affinity resin from which less ligand will leach during purification of a molecule to which the ligand binds. The methods entail contacting an affinity resin with a hydroxyalkyl amine compound. The affinity resin is composed of a ligand that is conjugated to a chromatographic support, and has been stored for at least 48 hours after coupling the ligand to the chromatographic support. The affinity ligand is incubated in the presence of the hydroxyalkyl amine compound for a time sufficient to remove ligand that is not stably bound to the chromatography resin. Sufficient unstably bound ligand is removed by the treatment so that when the treated affinity resin is used for affinity purification of a molecule to which the ligand specifically binds, less ligand leaches from the affinity resin as compared to a purification of the molecule on the affinity resin that has not been treated with the compound.

BRIEF DESCRIPTION OF THE DRAWINGS

FIG. 2 shows that bulk ethanolamine washes can bring down the amount of Mu-IgG that leaches from the column. A single lot of immunoaffinity resin was used for this study. Here, the percent recovery of FVIII (Factor VIII) was assessed for varying lengths of wash time (varying number of one-hour washes) used for the ethanolamine treatment. For each sample of washed resin, the FVIII challenge in column format (load/wash/elution) was performed three times, except BW-3X (3×1 h) which was only run twice. The last bar in each group is the mean percent (%) recovery for all three runs. Numbers above the bars indicate the units of FVIII which were loaded per ml of resin for each run. The goal was to load 250–350 U/ml resin. For the control (0 h), BW-1Xb (1 h), BW-2X (2 h), and BW-3X (3 h) columns, the percent recoveries obtained (40–48%) were within the range of the usual percent recovery seen without ethanolamine washing. The percent recoveries from the column prepared with resin which was washed overnight, BW-ON, (18 h) were somewhat lower (28–38%).

FIG. 5 shows a comparison of the levels of Mu-IgG removed with 20 column volumes (CV) of 1 M ethanolamine, 0.2 M sodium bicarbonate pH 8.5. Each lot of test resin was washed with 20 CV of buffered 1 M ethanolamine, pH 8.5 at 2–8° C. Control runs done with Resin lot 028 were also run with 20 CV of buffered ethanolamine at 2–8° C., as well as buffer consisting of only 0.2 M bicarbonate at pH 8.5. Data from a previous study are also included for comparison ("28 RT wash") where resin lot 028 was washed-in-place with 20 CV of buffered 1 M ethanolamine, pH 8.5, at ambient temperature. As seen from the 028 RT wash data, the uppermost line on the graph, washing at ambient temperature is 10 times more effective at removing Mu-IgG than washing at 2–8° C. (200 ng/ml vs. 20 ng/ml at 2–8° C.). On the legend, the number of days indicates how long the column sat at 2–8° C. before being washed. This number affects the Mu-IgG concentration of only the "CV1–4" samples.

DETAILED DESCRIPTION

DEFINITIONS

The term "alkyl," by itself or as part of another substituent, means, unless otherwise stated, a straight or branched chain, or cyclic hydrocarbon radical, or combination thereof, which may be fully saturated, mono- or poly-unsaturated and can include di- and multivalent radicals, having the number of carbon atoms designated (i.e., $C_1$–$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)ethyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butenyl, and the higher homologs and isomers. Alkyl groups which are limited to hydrocarbon groups are termed "homoalkyl" A "straight chain alkyl amine" is a linear (i.e., unbranched) alkyl group with an amine moiety.

A "chromatographic support" refers to a solid or semi-solid support to which a ligand can be attached. The chromatographic support is suitable for use in column chromatography or other types of purification.

The phrase "activated hydroxyl containing support" refers to a chromatographic support or matrix, etc., that contains hydroxyl groups that have been derivatized with a chemical moiety that make the hydroxyl more reactive with a ligand.

The phrase "cyanogen bromide activated resin" refers to a chromatographic support that contains cyanate esters or a chromatographic resin that has been reacted with cyanogen bromide or a cyanylating agent(s).

An "affinity resin" or an "affinity chromatography resin" refers to a chromatographic support to which a ligand is attached. The ligand can be any molecule that specifically binds to a molecule of interest which is to be purified or subtracted from a mixture. For use in affinity purification, the ligand is coupled to the chromatographic support. An example of a ligand is an antibody that binds specifically to the molecule being purified. Ligands are available which bind to a wide variety of molecules, including, for example, proteins, polypeptides, peptides, carbohydrates, nucleic acids, organic and inorganic molecules, and the like.

An "antibody" can be derived from sequence of a mammal, non-mammal (e.g., birds, chickens, fish, etc.), or fully synthetic antibody sequences. A "mammal" is a member of the class Mammalia. Examples of mammals include, without limitation, humans, primates, chimpanzees, rodents, mice, rats, rabbits, sheep, and cows. The term "antibody" also refers to fragments and substitutes for antibodies such as $F(ab')_2$, Fab', and Fab fragments. Additionally the "antibodies" can be single chain antibodies known as ScFv fragments, which are obtained by recombinantly fusing the variable regions of the light and heavy chains of the antigen binding fragment of interest.

The phrase "specifically (or selectively) binds to" or "specifically (or selectively) immunoreactive with", refers to a binding reaction which is determinative of the presence of the molecule of interest in the presence of a heterogeneous population of proteins and other biologics. Thus, under designated assay conditions, the specified ligands (e.g., an antibody) bind to a particular molecule (e.g., an epitope) and do not bind in a significant amount to other molecules present in the sample. Antibodies raised against a multivalent antigenic polypeptide will generally bind to the proteins from which one or more of the epitopes were obtained. Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See Harlow and Lane (1988) *Antibodies, A Laboratory Manual*, Cold Spring Harbor Publications, New York "Harlow and Lane"), for a description of immunoassay formats and conditions that can be used to determine specific immunoreactivity. Typically a specific or selective reaction will be at least twice background signal or noise and more typically more than 10 to 100 times background.

The term "purified" refers to an enriching for, or depleting of, a particular molecule from a mixture of molecules. The term "purified" does not necessarily indicate that complete purity or complete removal of the particular molecule has been achieved during the process.

I. INTRODUCTION

The present invention provides methods and compositions for decreasing the amounts of ligand (e.g., antibody, protein, etc.) that leach from a chromatography resin (e.g., an affinity resin) during purification of a molecule (e.g., peptide, protein, Factor VIII, etc.). One particular drawback to the use of, for example, cyanogen bromide chemistry in generating chromatography resins is that during storage or use, the ligand often leaches from the chromatographic support, especially if the ligand is a protein such an antibody (Berry and Pierce, supra; Antonsen et al. (1991) Biotechnol. Prog. 7: 159–172; van Sommeren et al. (1993) J. Chromatogr. 639: 23–31; Ubrich and Rivat (1996) Art. Cells, Blood Subs., and Immob. Biotech. 24: 65–75). The leaching of a ligand from a chromatography resin presents particular problems in the preparation of a pharmaceutical that is being purified using the resin.

The methods of the present invention, however, decrease the amount of ligand that leaches from a chromatography resin, resulting in a savings of time, money, effort and a product that can meet the stringent regulatory guidelines for the presence of ligand. Therefore, the invention provides significant advantages over previously available methods using chromatography to purify a pharmaceutical or other compound.

Briefly, the methods of the invention involve contacting a chromatography resin with an alkyl amine compound that includes at least one hydroxyl moiety. The treatment of the affinity column with the compound decreases the amount of ligand that leaches from the column during purification of a desired molecule. These methods and compounds will be described in more detail below.

Although the methods are described herein primarily in the context of conditioning affinity resins, the methods are equally applicable to other types of resins that have a binding moiety attached to a chromatographic support. For example, the binding moiety can be a charged group, in which case the resin is useful for ion exchange.

II. METHODS OF PREPARING AFFINITY COLUMNS

Affinity chromatography and related techniques provide powerful methods for the enrichment and purification of molecules from a heterogeneous mixture (for a review, see Scopes, R. K. (1982) Protein Purification, Principles and Practice, pp. 111–135). In general, affinity columns contain a chromatographic support to which is coupled a ligand. The ligand has an affinity for the molecule that is being purified or depleted from a mixture of compounds. By virtue of this affinity and with careful washing of the affinity resin with various buffers the molecules of interest, in a mixture of molecules applied to the resin, will bind to the ligand while other molecules in the solution will flow through the column or remain free in solution if performed in batch mode. The molecule being purified can then be eluted from the resin, resulting in an enrichment of the molecule.

A wide variety of affinity chromatography media and methods for making them are known in the art. Affinity chromatography media include, but are not limited to, dye ligand resins, DNA ligand resins, peptide ligand resins, small organic molecule resins (organic molecules under 50 kDa), immunoaffinity resins, etc. The syntheses of many affinity resins involve coupling the ligand of interest to a matrix or solid support, such as a polysaccharide solid support (e.g., Sepharose, agarose, etc.).

Typically the ligands are coupled through covalent bonds to functional groups or derivatized functional groups on the chromatographic support. Many chromatographic matrices, (e.g., Sepharose, agarose, etc.) contain an abundance of available hydroxyls. The hydroxyls on most unmodified supports, however, are fairly weak nucleophiles, but can be derivatized by reacting them with an activating reagent. The resulting activated hydroxyl resin can be reacted with the ligand to form an affinity resin. A variety of activating compounds and schemes are known in the chromatographic art, such as 1,1'-carbonyldiimidazole, toluene sulfonyl chloride (tosyl chloride), and 3,3,3-triflouroethanesulfonyl chloride (tresyl chloride).

Perhaps the most widely used activation methods are those that involve cyanogen bromide and other reagents which generate cyanate esters on the chromatographic supports (for a review of cyanogen bromide coupling technologies, see Kohn and Wilchek (1984) Applied Biochem. and Biotechnol. 9: 285–305). In methods using cyanogen bromide, the hydroxyls on a support, e.g., agarose, are activated by contacting the matrix with cyanogen bromide (CNBr) at an alkaline pH to form a cyanate ester (Kohn and Wilchek, supra; March et al. (1974) Anal. Biochem. 60: 149–152). These cyanate esters are then reacted with a nucleophile on the ligand to couple the ligand to the chromatographic support. In the case of a protein, typically the nucleophile is a primary amine. Several products have been described as being formed between the amine and the cyanate ester: a isourea derivative of the ligand, a carbamate ester, a linear imidocarbamate, and a cyclic imidocarbamate (Kohn and Wilchek, supra; Jennissen (1995) J. Mol. Recog. 8: 116–124).

The unreacted cyanate esters are typically blocked with a low molecular weight amine, such as ethanolamine or glycine (Desai (1990) J. Chem. Tech. Biotechnol. 48: 105–126; Berry and Pierce (1993) J. Chromatog. 629: 161–168). These amines can also decrease non-specific amino ion exchange properties of the resin by releasing the isourea derivatives as substituted guanidines (Wilchek et al. (1975) Proc. Natl. Acad. Sci. U.S.A. 72: 1055–1058).

The ligands that are coupled to the solid support can take a wide variety of forms. For example, affinity columns containing lectins, avidin, Staphylococcal protein A, biotin labeled proteins, and Fv fragment for hen egg white lysozyme (Berry and Pierce, supra.) as ligands have been used to purify glycoproteins, immunoglobulins, biotin labeled proteins and hen egg lysozyme, respectively. Antibodies that specifically bind to the molecule being purified have been used as ligands on cyanogen bromide activated chromatographic supports (Desai (1990) J. Chem. Tech. Biotechnol. 48: 105–126; Berry and Pierce, supra.). Methods for preparing polyclonal and monoclonal antibodies are known in the art (See generally, Harlow and Lane, supra.).

III. TREATMENT OF CHROMATOGRAPHY RESINS TO DECREASE LIGAND LEACHING

The invention provides methods of conditioning a chromatography resin to reduce or eliminate leaching of ligand from the resin. The methods involve contacting the affinity resin with an effective amount of one or more alkyl amine compounds that have at least one hydroxyl moiety for a sufficient time to remove ligand that is not stably bound to the chromatography matrix. Ligand that is not stably bound to the chromatographic support would, if not removed from the resin, be susceptible to leaching from the resin during use of the chromatography resin to purify a molecule of interest.

During storage of an affinity resin, for example, the amount of unstably bound ligand can increase, due to hydrolysis of isourea or carbamate bonds from insufficiently cross-linked ligands, such as antibodies. The isourea linkage is less stable than the desired carbamate linkage (and other linkages), and therefore is more susceptible to leaching of ligand when the resin is used. The isourea bond, however, can be displaced by amine containing compounds, which can include the molecule being purified. Because the leaching problem is generally more acute after an affinity resin has been stored after coupling of the ligand and prior to use, the methods of the invention are typically employed after an affinity chromatography resin has been stored for a period of time. Generally, the methods are employed at least about two days after the ligand was coupled to the chromatographic support. The period of storage between the coupling and the wash can be one week or longer, one month or longer, or even one year or longer.

To achieve the desired amount of leaching reduction, the affinity resin is generally incubated in the presence of the hydroxyalkylamine compound for at least about 30 minutes. More preferably, the incubation period is at least about one hour, and still more preferably at least about two hours. The time of incubation is generally less than about eighteen hours, more preferably is less than about eight hours, and still more preferably is less than about three hours. Further reduction in leaching can be achieved by repeating the incubation with the hydroxyalkylamine compound one or more times. In an example of a presently preferred embodiment, the affinity resin is subjected to two one-hour incubations in the hydroxyalkylamine compound.

Hydroxyalkyl amine compounds that are suitable for use in the methods of the invention include, for example, ethanolamine, ethanolamine, propanolamine, butanolamine, and the like. Ethanolamine is an example of a presently preferred compound. Other suitable compounds include, for example, glycine, tris(hydroxymethyl)aminomethane ("Tris"), as well as other hydroxyl-containing amino acids such as serine and threonine.

A concentration of hydroxy alkyl amine compound that is sufficient to achieve the desired reduction in leaching of a ligand from a chromatography matrix is referred to as an "effective amount" or an "effective concentration." For use in the methods of the invention, the hydroxyalkyl amine compound is generally formulated in a solution at a concentration of at least about 500 mM, more preferably at least about 750 mM, and still more preferably at least about 900 mM. The concentration of the hydroxyalkyl amine compound is generally less than or equal to about 1.5 M, more preferably less than or equal to about 1.2 M, and still more preferably the compound is present at a concentration of less than or equal to about 1.0 M.

The hydroxyalkyl amine compound is generally present in a buffered solution when contacted with the chromatography resin. The pH of the solution is typically at least about 7, more preferably at least about 8, and still more preferably at least about 8.2. The pH of the solution is generally less than about 11.5, more preferably less than about 9, and still more preferably less than about 8.7. Suitable buffers for use in formulating the compound include, for example, sodium bicarbonate, tris(hydroxymethyl)aminomethane ("Tris"), Bis-Tris, CAPS, CAPSO, CHES, etc.

Figure 8:
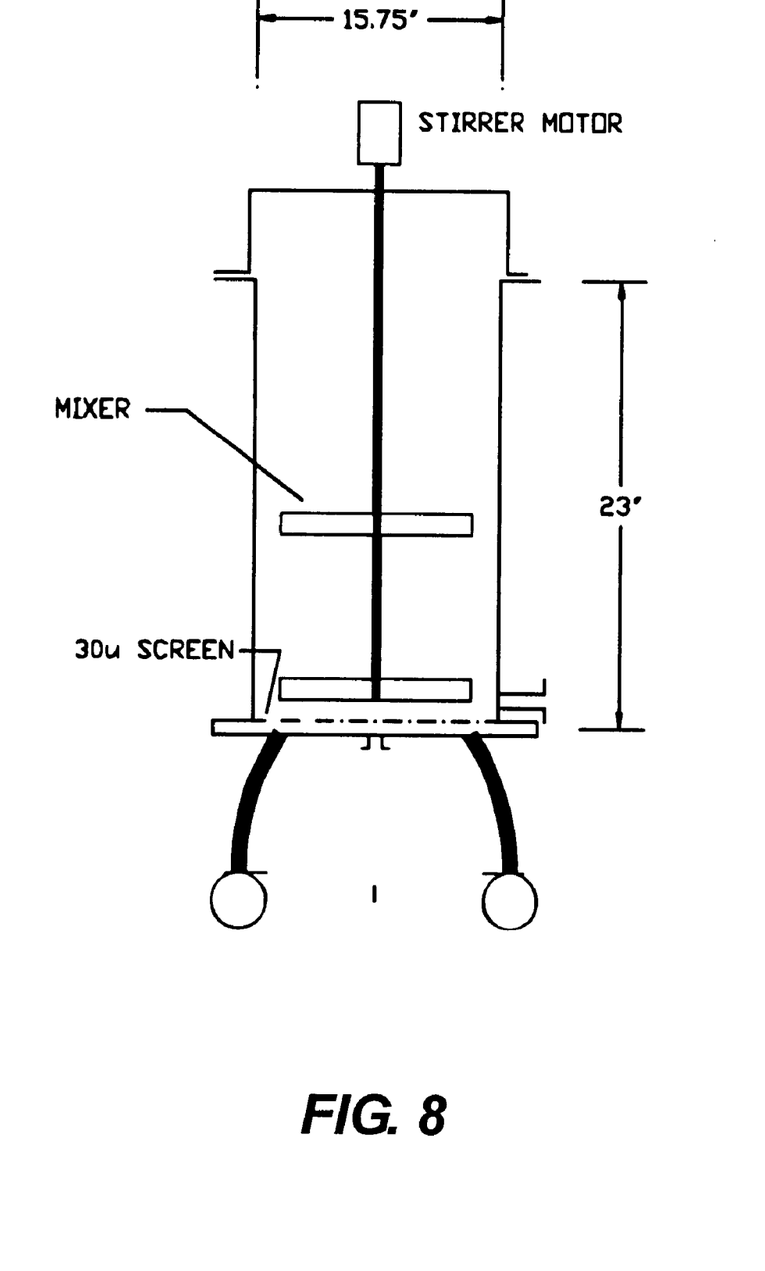
FIG. 8 shows the design of a wash vessel for bulk washing of affinity resin. Resin is added to the vessel through the openings at the top of the tank. The tank is fitted with a 30 micron stainless steel screen on the bottom. The screen permits the retention of the resin, while allowing the buffer to pass through. Buffers are evacuated through the port at the bottom of the tank, and resin is removed from the tank using the port coming from the side of the tank. The vessel is also equipped with a variable speed agitator at the top.

The contacting of the chromatography resin with the solution of hydroxyalkyl amine compound can be in a column (a wash-in-place format) or in batch (bulk) mode. The bulk washing of resin facilitates the washing of large amounts of resin in a short amount of time. In addition, bulk washing can, in some cases, be more efficacious than a wash-in-place format. An example of a wash vessel suitable for performing bulk washes is depicted in FIG. 8. The wash vessel is a cylindrical container having a mixer attached to a stirrer motor. The vessel includes ports for the addition and removal of the buffer as well as removal of the resin.

The chromatography resin is generally incubated in the presence of the hydroxyalkyl amine compound at a temperature of between about 2° C. and 37° C. Ambient room temperature (e.g., 20–25° C.) is a presently preferred temperature range.

After incubating the chromatography resin with the hydroxyalkyl amine compound, the chromatography resin can be washed one or more times with water or an appropriate buffer. Preferably at least two washes are performed. The chromatography resin is then equilibrated with an appropriate buffer for the purification, after which the resin is then used in the usual fashion.

One example of a preferred method of treating an affinity resin to reduce leaching of ligand is as follows. Ethanolamine (2-aminoethanol) is used as the hydroxyalkyl amine compound. When present at a concentration above 500 mM, and more preferably around 1 M, ethanolamine exhibits a surfactant activity and is effective at dislodging unstably bound ligand from the affinity resin so that when the resin is used for purification of a pharmaceutical compound, less ligand is present in the end product. The ethanolamine is typically buffered with 0.2 M sodium bicarbonate. The pH of the ethanolamine solution is preferably between 7 to 11.5, more preferably from 8 to 9, and still more preferably from 8.2 to 8.7. More effective removal of unstably bound ligand can be achieved by formulating the ethanolamine in a tris(hydroxylmethyl)aminomethane ("Tris") solution. The affinity resin is preferably incubated in the presence of the ethanolamine for two one-hour periods.

EXAMPLES

The following examples are offered to illustrate, but not to limit the claimed invention.

Example 1

Washing of Stored Resin with Ethanolamine to Decrease Leaching of anti-FVIII MAb This example describes the final steps in the preparation of anti-FVIII monoclonal antibody (MAb) resins and the subsequent treatment of the resins with ethanolamine to decrease leaching of the anti-FVIII antibody. The anti-FVIII MAb (Mu-IgG) resins were formed with anti-Factor VIII MAb that was reacted with cyanogen bromide treated Sepharose CL-4B. In the final steps of the manufacturing process, the resin was washed with 1% (0.16 M) ethanolamine (2-aminoethanol) after the coupling reaction to block unreacted cyanate esters. The resin was then washed with Buffer #1, 50 mM Tris, 0.15 M NaCl, pH. 7.2, and stored in that Buffer #1 containing 0.01% thimerosal as a preservative. Later, the resins were removed from storage and used in the experiment.

1.0 INTRODUCTION

A buffer containing ethanolamine was tested as a process improvement to reduce the levels of murine immunoglobulin (Mu-IgG) that specifically binds to Factor VIII (FVIII) that leach from the immunoaffinity resin during FVIII purification.

In this example, we have tested the efficacy of an ambient temperature ethanolamine buffer batch wash method. For all experiments in this example, an ethanolamine concentration of 1 M in 0.2 M sodium bicarbonate, pH 8.5, was used as the wash buffer.

First, we determined the optimal number of ethanolamine batch wash treatments. Aliquots of resin were treated serially in increments of one hour, using one resin volume of fresh 1 M ethanolamine wash buffer each hour, to determine the optimal blocking time. Samples of the spent ethanolamine wash buffer were stored at 2–8° C. and assayed for Mu-IgG (see below for Mu-IgG assay).

Next, scale-down chromatography was performed to evaluate the binding capacity of the immunoaffinity resin for FVIII after the ethanolamine treatment. Aliquots of treated resin were packed into 5 ml columns. The columns were loaded with FVIII cell culture supernatant and evaluated for two parameters: FVIII binding capacity (percent recovery) and Mu-IgG levels in the eluates. In addition, a Mu-IgG/FVIII ratio was calculated for the pooled elution fractions. The recovery of FVIII from the washed resin was determined by chromogenic assay to establish that resin function was not decreased as a result of the more stringent ethanolamine treatment. The ratio of Mu-IgG to FVIII was calculated to determine whether contaminant levels in the final product were sufficiently reduced following ethanolamine treatment.

2.0 METHODS 2.1 Description Of The Bulk Wash Ethanolamine Treatment

In order to determine the optimal time and number of ethanolamine treatments, five 7 ml samples from the resin lot were tested. Four samples were washed for varying lengths of time (1 h, 2×1 h, 3×1 h, and 1×8 h (also called the overnight sample, designated ON)). One aliquot of resin was left untreated as a control. Since the buffer-to-resin ratio is 2:1, fourteen ml of resin slurry were pipetted into a sintered glass vacuum filter to obtain 7 ml of resin for blocking treatment. Buffer #1, 50 mM Tris, 0.15M NaCl, 0.01% thimerosal, pH 7.2, was removed via vacuum and subsequently, samples were taken of the removed Buffer #1 and stored at 2–8° C. until they could be analyzed for Mu-IgG by the IGEN Origen system assay (see below).

Seven ml of Ethanolamine Wash Buffer (1M ethanolamine, 0.2M Na Bicarbonate, pH 8.5) were added to the filter in order to reslurry the resin, which was then pipetted into a 15 ml polypropylene tube. The tube was placed on a rocker for 1 hour (or 18 hours for overnight sample) at ambient temperature (18–22° C.). At the end of one hour, the slurry was poured into the sintered glass filter and the ethanolamine buffer was removed. Samples from the spent ethanolamine buffer washes were stored at 2–8° C. to be tested for Mu-IgG concentration. Resin samples that were washed for a total of two or more hours were drained each hour and received serial additions of one resin volume of buffered ethanolamine. After the final ethanolamine wash, resin was reslurried in Buffer A (0.02 M HEPES, 0.02 M $CaCl_2$, 1 M NaCl, 0.1% Tween-80, 0.01% thimerosal, pH 7.0 (±0.2)), pipetted into 15 ml tubes and stored at 2–8° C.

2.2 Chromatography Details: Test Of FVIII Binding

The chromatography methods were controlled and executed using the Pharmacia AKTA™ FPLC at 2–8° C. Bed height (6 cm) and linear flow rate (45 cm/hr) were kept constant. All chromatography steps were performed in the forward direction except for the elution which was done in reverse.

Treated resin was packed into 5 ml scale-down HR columns and challenged with cell culture supernatant (CCS) composed of Gibco BRL CHOR5 media and CHO cells transfected with an FVIII clone that was used to generate FVIII used to obtain the anti-FVIII monoclonal antibody. Standard hybridoma techniques were used to generate and screen for the anti-FVIII MAbs. The anti-FVIII monoclonal antibody was coupled to a Sepharose CL-4B resin.

The CCS contained approximately 1 U FVIII/ml. The desired amount of FVIII cell culture supernatant loaded onto the columns was in the range of 250–350 U FVIII per ml of resin for all runs. Three purification runs were performed on each column of washed resin. The columns were first washed with Buffer B (20 mM HEPES, 20 mM $CaCl_2$, 1.0 M NaCl, 0.1% (v/v) Tween-80, pH 7.0 (±0.2)). Then the columns were loaded with FVIII containing material, and washed twice with Buffer E (20 mM MES, 20 mM $CaCl_2$, 1 M NaCl, 0.1% Tween-80, pH 7). Then the columns was developed with Buffer C (500 mL/L ethylene glycol, 20 mM $CaCl_2$, 20 mM histidine, 0.25 M NaCl, 0.01% Tween-80, pH 7.0 (±0.2)). Fractions were taken of the chromatography runs and were tested for Mu-IgG levels (IGEN) and FVIII activity (Chromogenix, COATEST® FACTOR VIII).

2.3 Coatest® Chromagenic FVIII Activity Assay

A chromogenic FVIII activity assay (Chromogenix) was used to estimate the concentration of FVIII in load, wash and elution fractions from each scale-down immunoaffinity column. The activity assay for FVIII function was performed using a Chromogenix kit, and a World Health Organization "Mega" FVIII Standard. A conversion factor of 200 ng per Unit FVIII was used for calculations.

2.4 Murine IgG Assay

The Mu-IgG assay was performed using an IGEN Origen analyzer. The assay involves the formation of an immune complex made up of two anti-murine immunoglobulin antibodies labeled with TAG (a ruthenium chelate) or biotin that binds to Mu-IgG in solution. Upon addition of a substrate for the TAG, the complex generates an electrochemiluminescent signal that can be detected by an IGEN Origen analyzer and, through comparison to a standard curve, one can quantitate the concentration of Mu-IgG in test samples. The assay was used to quantitate the Mu-IgG concentration in the various column fractions of the FVIII purification.

2.5 Ratio of ng Mu-IgG per 100 $\mu$g FVIII

In order to determine whether Mu-IgG levels had been sufficiently reduced, Mu-IgG/FVIII ratios were calculated for each FVIII purification run. Low ratios would indicate the resin would have been adequately washed and allow us to determine which washing procedure was most effective.

3.0 DISCUSSION

Figure 1:
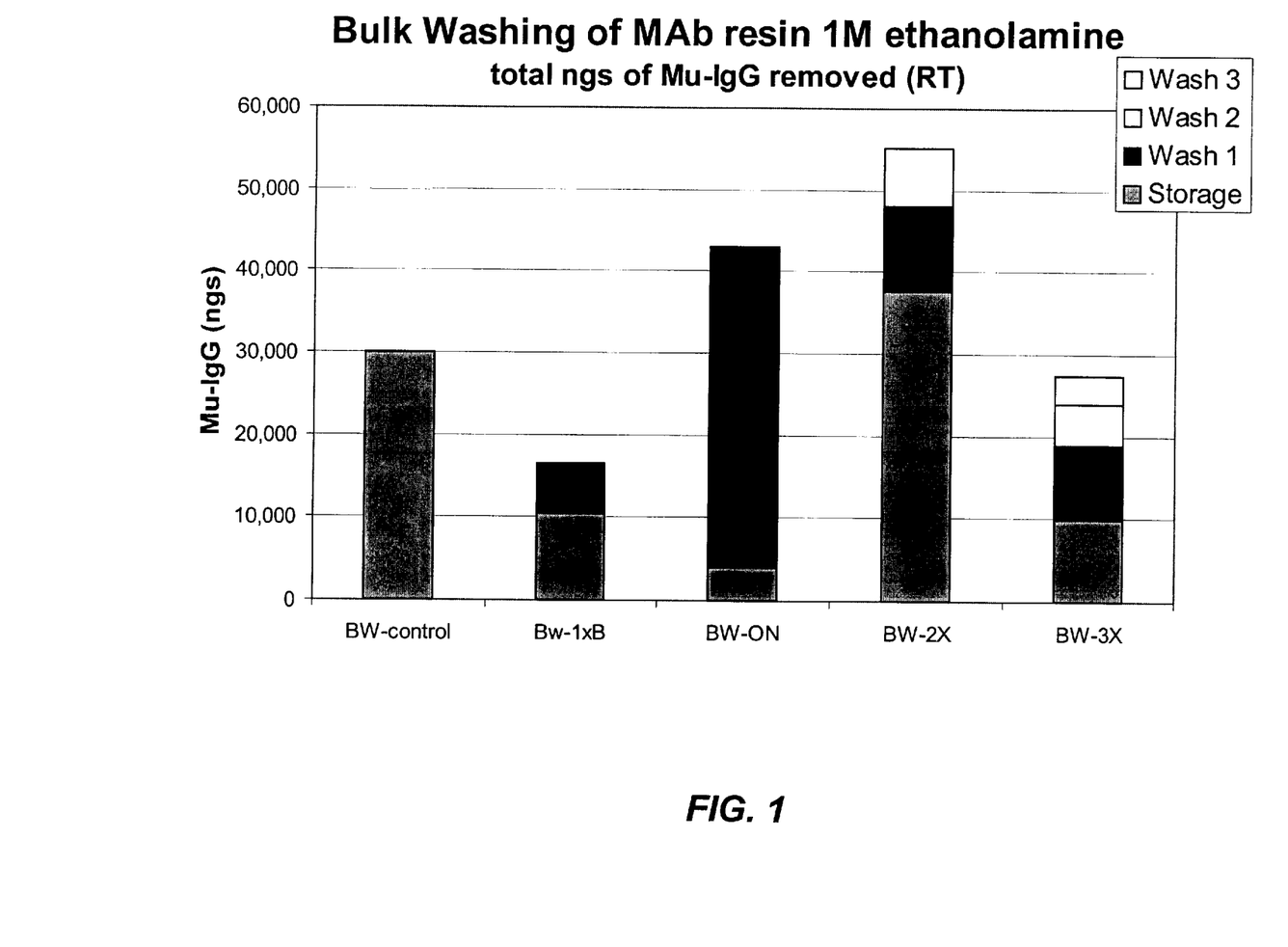
FIG. 1 shows that buffered ethanolamine washes (1 M ethanolamine in sodium bicarbonate pH 8.5) are effective in removing Mu-IgG (anti-Factor VIII MAb) from the Mu-IgG—Sepharose CL-4B resin. The wash steps are presented in a cumulative format with each serial wash removing additional Mu-IgG. The BW-1Xb, BW-2X and BW-3X nomenclature indicate that the resin was bulk-washed with one, two or three one-hour washes respectively.

FIG. 1 shows the amount of Mu-IgG (ng) that can be removed with various bulk-wash treatments before FVIII challenge. The bars represent cumulative amounts of Mu-IgG, and it can be noted that additional small increments of Mu-IgG are removed with each serial wash. The amount of antibody removed by the serial ethanolamine washes is small compared to the total amount of coupled antibody, but it is significant in terms of the allowable amount of leachate specified in production. A single wash removed about 7 micrograms from a 5 ml (5 mg) resin sample, which corresponds to about 0.14%. Two ethanolamine washes removed an average of 4.5 micrograms from the 5 mg sample, or about 0.09%. The buffered ethanolamine solution removed 10-fold more Mu-IgG than the following buffers tested: a) 50% ethylene glycol, 25 M NaCl, pH 7; b) 50 mM glycine, pH 2.8; c) 0.1 M NaOAc, 0.5 M NaCl, pH 4; d) 0.2 M glycine, pH 8; e) 0.02 M HEPES, 0.02 M $CaCl_2$, 1 M NaCl, 0.1% Tween 80, pH 7; f) 0.1 M $NaHCO_3$, 0.5 M NaCl, pH 8.3; and g) 20 mM MES, 1 M NaCl, 0.1% Tween 80, pH 6. Washes with 1 M ethanolamine in tris(hydroxylmethyl) aminomethane (pH 8.5) were 1.5–3 times more effective at removing Mu-IgG than 1M ethanolamine buffered in 0.2 M sodium bicarbonate (pH 8.5).

Figure 2:
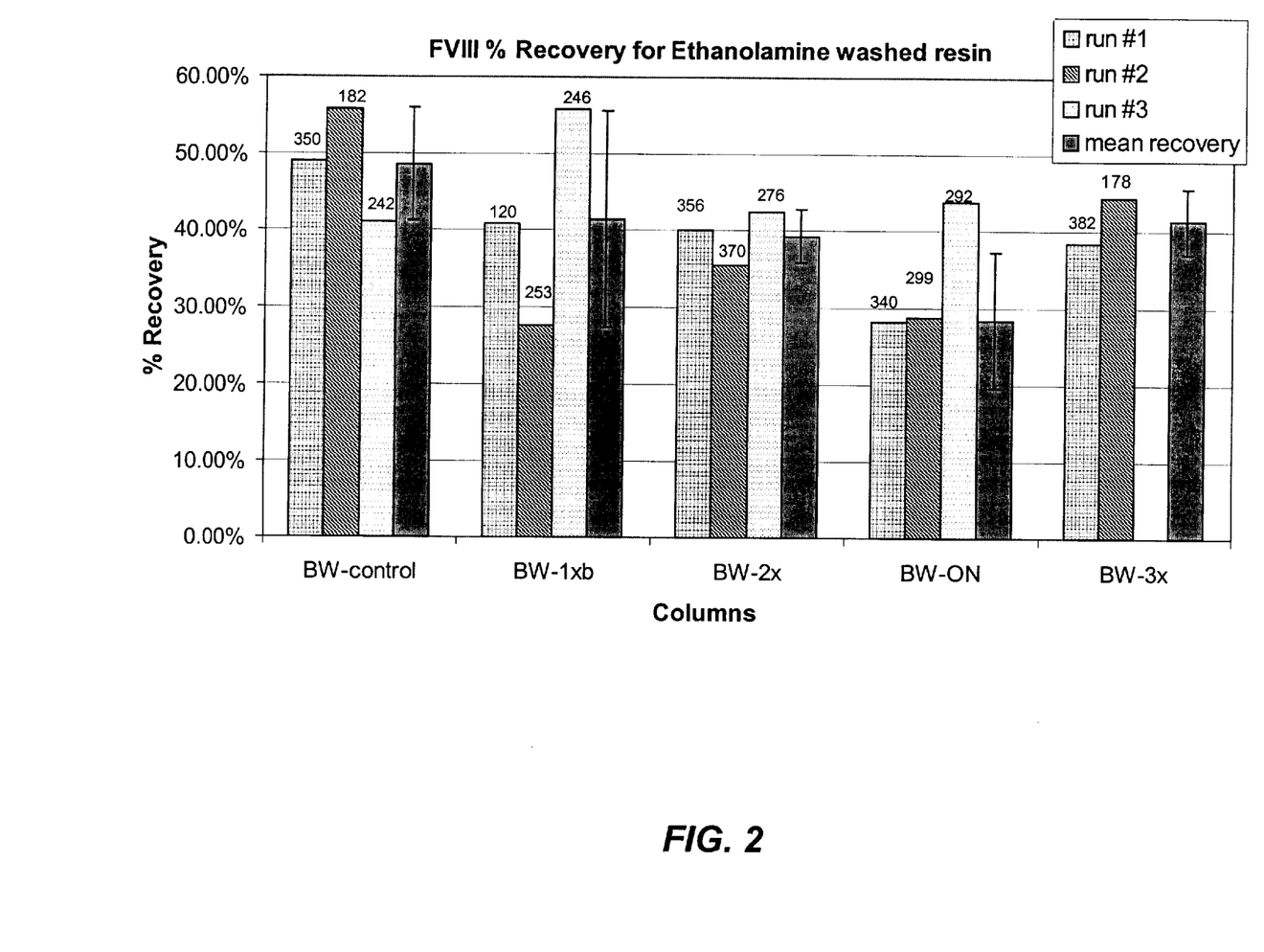

FIG. 2 shows the percent recovery of FVIII from experiments performed with the 5 ml columns that contained bulk-washed (BW) resin. The bulk wash treatment with ethanolamine for up to 3 hours of treatment does not reduce the capacity of the MAb resin for binding FVIII. Triplicate FVIII load/elution cycles were performed with each column for each wash condition. In FIG. 2, the fourth bar in each data set is the arithmetic mean, or average, shown with the standard deviation (error bar). When comparing the averages for the 1×, 2× and 3× wash conditions, the error bars overlap with the average for the untreated control sample value for FVIII percent recovery, indicating no loss in binding capacity. For the control, 1× wash, 2× wash and 3× wash resin, the FVIII recovery averages 40–48%. Variability between runs is within the 10–15% experimental error accepted for the COATEST® assay. However, it can be seen that the average percent recovery data for the 18 hour (ON) treated data set is lower (around 30%) than for the shorter ethanolamine treatments, indicating some loss of FVIII binding function as a result of the longer treatment. A possible explanation is that 18 hours (ON) at an elevated pH of 8.5 could be unfavorable for the anti-FVIII antibody, thus resulting in lower product recovery.

Three serial tests (FVIII purification runs) were performed on each column, with a fresh FVIII load applied every three days. The goal was to load 250–350 units each time, and twelve out of fourteen runs were within that range. The numbers above the bars in FIG. 3 indicate the units of FVIII which were loaded per ml of resin for each run.

Figure 3:
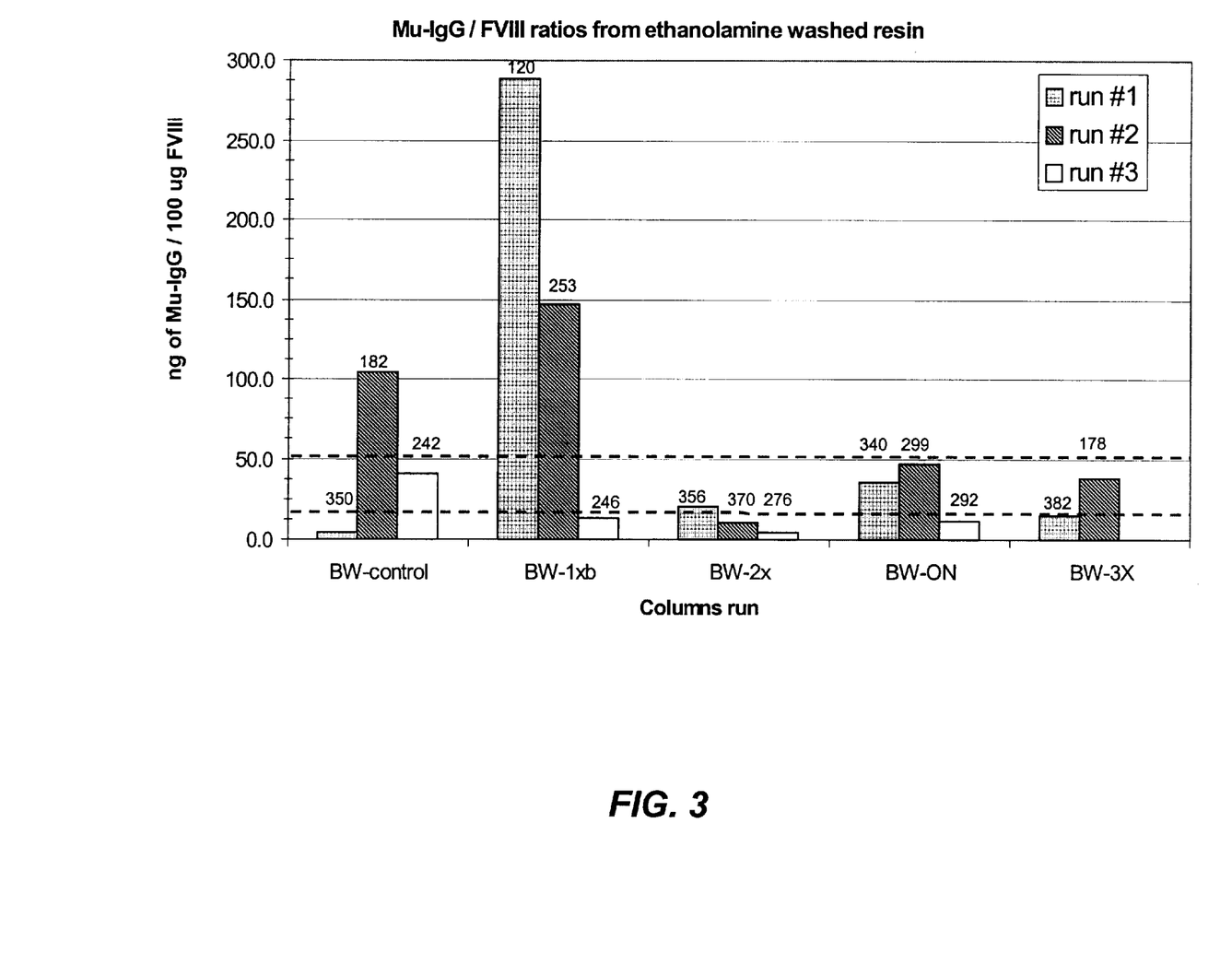
FIG. 3 shows the Mu-IgG/FVIII ratios for each of the FVIII challenge runs.

In FIG. 3, the Mu-IgG/FVIII ratios are presented for four treated samples compared to an untreated control. The visual difference between the 2× washed sample and either 1× or untreated resin samples is striking. The 1× bulk-washed and untreated control samples have much higher (less acceptable) IgG/FVIII ratios The 3× bulk-washed resin (BW-3X) was only tested twice. Because there was not a significant improvement in the ratios produced by the longer BW-3X treatment and the FVIII capacity was diminished for the ON sample, we did not test the 3× wash further.

4.0 CONCLUSIONS

The bulk washing method performed at ambient temperature was effective in removal of 200 ng/ml Mu-IgG per resin volume. For a one-hour treatment this method removed about 7 micrograms out of a total of 5 milligrams of Mu-IgG in the resin, or about 0.14% of Mu-IgG in the resin sample.

Two one-hour bulk-wash treatments gave the optimum result, i.e. the maximum removal of Mu-IgG with the minimum number of washes without decreasing the antigen binding capacity (FVIII). Thus, this example indicates that treatment of an affinity resin that has been stored with 1 M buffered ethanolamine in bicarbonate buffer for two one-hour batch washes, and then washed with (six) resin volumes of ultrapure water is an effective method for reducing leaching of ligand.

The bulk wash treatment with 1 M ethanolamine in bicarbonate buffer did not reduce the capacity of the MAb resin for binding FVIII. Immunoaffinity resin which was treated for one, two or three hours with 1 M buffered ethanolamine did not lose any FVIII binding capacity compared to control (untreated) resin. Reasonable (40–48%) percent recoveries were obtained from all samples tested.

Resin samples which were treated for long periods of time (18 h) with buffered ethanolamine, pH 8.5, did lose some binding capacity. The percent recovery of FVIII ranged from 28–38% for those resin samples.

Example 2

Feasibility Study of Wash-in-Place Method with 1.0 M Buffered Ethanolamine at 2–8° C. to Reduce Mu-IgG Leaching This Example tested the effectiveness of a wash-in-place protocol for reducing leaching of antibody from an affinity resin using a buffer that contains 1M ethanolamine, 0.2 M sodium bicarbonate pH 8.5. This buffer was effective in removing loosely bound or aggregated antibody from an affinity resin when used in a bulk washing format at ambient temperature in Example 1. The new ethanolamine buffer was able to remove loosely bound or aggregated antibody, as well as displace, through nucleophilic substitution, unstable isourea complexes remaining from the cyanogen bromide (CNBr) activation reaction. The goal of the present example was to determine whether the same buffer would be effective when used to treat resin in a wash-in-place format at lower temperature.

1. INTRODUCTION

A wash-in-place (IP) procedure was tested to determine whether it could reduce the levels of murine immunoglobulin (Mu-IgG) leaching from an immunoaffinity resin during FVIII purification. The designation WIP has been applied to model systems in which immunoaffinity resin was poured into a small scale column and washed in the column format.

One goal of the current study was to test the efficacy of 1M ethanolamine buffer in a WIP format at low temperature. A second goal was to determine the efficacy of other buffers in removing Mu-IgG from previously coupled resin.

2. STUDY OUTLINE

Nine lots of (unused) immunoaffinity resin that had been stored in Buffer #1 containing 0.01% thimerosal after coupling and blocking were used in this study. The Mu-IgG leaching status of eight of these lots was unknown. A wash-in-place method was used to remove any loosely or poorly bound Mu-IgG. By assaying samples of spent wash buffer for Mu-IgG concentration, it was possible to determine whether Mu-IgG leaching levels differ between the eight resin lots. Two sets of washing protocols were tested.

In part one of the study, a "mock elution" of each small-scale column (i.e. each resin lot) was performed. The intent was to test the efficacy of wash buffers for removing Mu-IgG. Any lot-to-lot differences in leaching behavior would be discerned, as higher leaching lots of resin would have higher concentrations of Mu-IgG in the wash samples. The mock elution consisted of five column volumes (CV) of Buffer A (0.02 M HEPES, 0.02 M $CaCl_2$, 1 M NaCl, 0.1% Tween-80, 0.01% thimerosal, pH 7.0 (+0.2)), followed by five CV of Buffer B (20 mM HEPES, 20 mM $CaCl_2$, 1.0 M NaCl, 0.1% (v/v) Tween-80, pH 7.0 (+0.2)), and four CV of Buffer C (500 mL/L ethylene glycol, 20 mM $CaCl_2$, 20 mM histidine, 0.25 M NaCl, 0.01% Tween-80, pH 7.0 (+0.2)). The columns were run at a linear flow rate of 45 cm/h. Samples of each wash were collected and assayed for Mu-IgG.

In part two of the study, the goals were to test the ethanolamine wash buffer (1 M ethanolamine, 0.2 M sodium bicarbonate, pH 8.5) in a wash-in-place format, determine whether there was a temperature effect on washing with 1M ethanolamine, and whether differences in Mu-IgG leaching levels were detectable between the lots of resin. Columns were washed in the cold (2–8° C.) with 20 CV of buffered 1M ethanolamine pH 8.5, 5 CV of Buffer B (20 mM HEPES, 20 mM $CaCl_2$, 1.0 M NaCl, 0.1% (v/v) Tween-80, pH 7.0 (±0.2)), and finally 5 CV of Buffer A (0.02 M HEPES, 0.02 M $CaCl_2$, 1 M NaCl, 0.1% Tween-80, 0.01% thimerosal, pH 7.0 (+0.2)). Every 4 CV of ethanolamine wash were pooled and then sampled along with the Buffer A and Buffer B fractions and submitted for Mu-IgG assay.

3.0 METHODS AND MATERIALS 3.1 Wash-in-Place Methods

All wash-in-place (WIP) procedures were controlled and executed using Unicorn software on the Pharmacia AKTA™ FPLC that was housed in a cold room (2–8° C.). Conductivity, absorbance, and pH were measured and data was stored on hard disk. Each lot of resin was packed into a 5 ml scale-down HR column and then treated with the WIP procedures. The chromatography parameters for the scale-down columns were matched to manufacturing specifications keeping the bed height (6 cm) and linear flow rate (45 cm/hr) constant.

3.2 Description Of "Mock Elution" Method

The AKTA™ FPLC method which ran the mock elution consisted of 5 CV of Buffer A, 5 CV of Buffer B, 4 CV of Buffer C, 5 CV Buffer B and 5 CV Buffer A. All runs were performed in the cold (2–8° C.). Samples were taken of the buffer that was used to store the resin (column packing), and Buffer A, B and C pools and submitted for Mu-IgG assay.

3.3 Description Of 1M Ethanolamine Wash-in-Place Method

A separate AKTA™ FPLC method was written for each lot of resin. The method consisted of running 20 CV of ethanolamine wash buffer (collected into 5×4 CV fractions), 5 CV of Buffer B, 4 CV of Buffer C and 5 CV of Buffer A. The Buffer A, B, and C washes were each collected as one pool. Samples from each of the 5 ethanolamine fractions and the pooled Buffer A, B, and C washes were taken and submitted for Mu-IgG assay.

3.4 MATERIALS

For these experiments, nine resin lots, from storage which were tested with the WIP protocols. Resin lot 028, a known high Mu-IgG leaching lot, was also tested as part of the nine lots. The composition of the test and control resins are shown in Table 1 specifying the lot of Anti-F8.1 Mu-IgG that was used in the coupling, as well as the age of the column post-coupling.

3.5 Murine IgG Assay

The Mu-IgG assay was used to determine Mu-IgG concentrations in samples and the assay method has been described in Example 1.

TABLE 1

| # | RESIN LOT | AGE OF RESIN (months) |
|---|---|---|
| 1 | 028 | 23 |
| 2 | 031 | 16 |
| 3 | 032 | 13 |
| 4 | 033 | 11 |
| 5 | 034 | 11 |
| 6 | 035 | 6 |
| 7 | 036 | 6 |
| 8 | 037 | 2 |
| 9 | 038 | 2 |

4.0 DISCUSSION AND RESULTS

Figure 4:
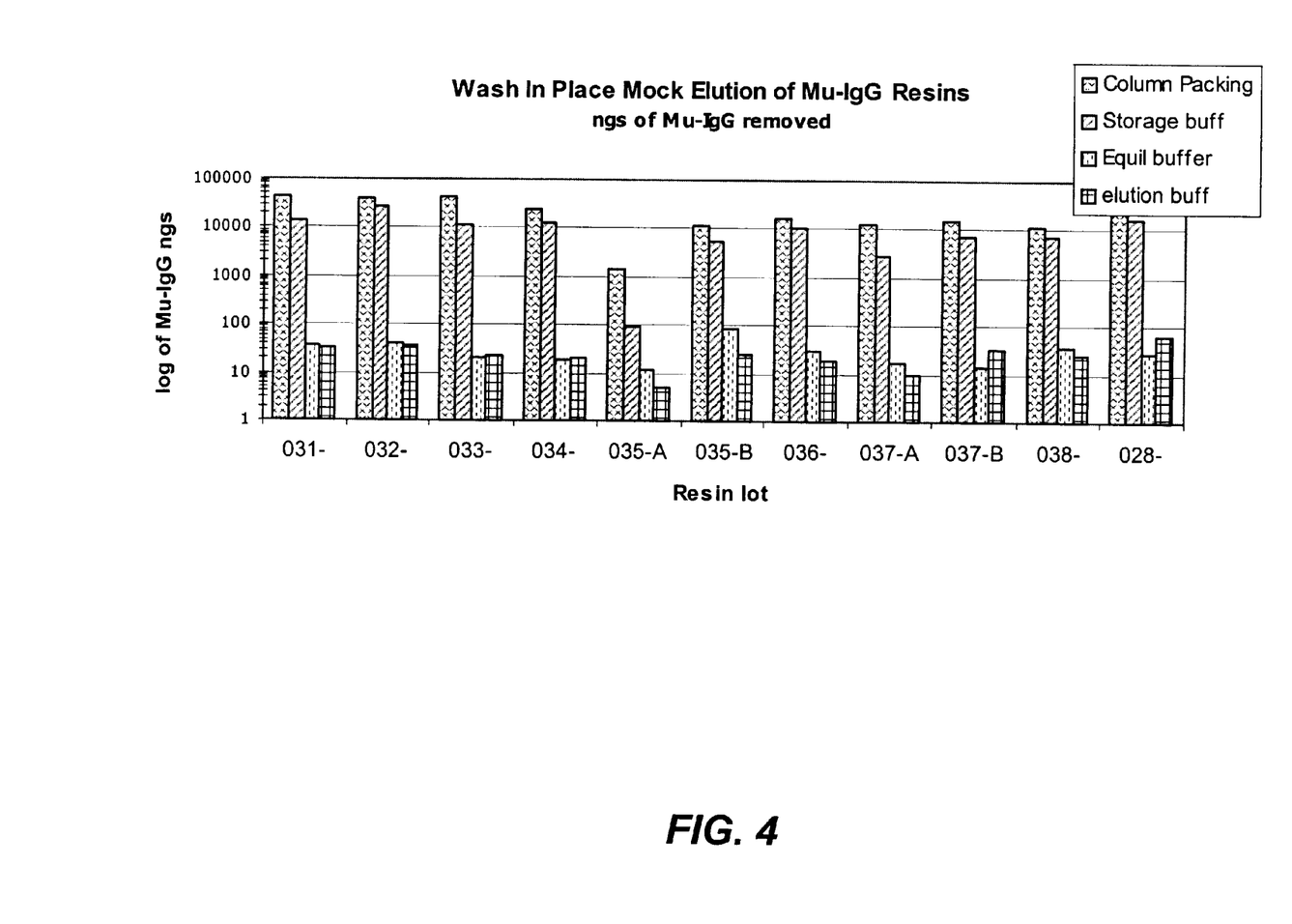
FIG. 4 shows that the mock Buffer B and Buffer C washes removed, on average, a total of 56 ng of Mu-IgG from each resin lot. The resins denoted 035A and 035B are duplicate runs on lot 035. Similarly, samples 037A and 037B are duplicate runs on the same sample—lot 037. The amount of Mu-IgG removed from each lot of resin was essentially equal and therefore the lots are indistinguishable from each other. The higher levels of Mu-IgG observed in the "Column Packing" and Buffer A samples are expected due to decoupling of Mu-IgG from the resin which occurs over time and reflects the fact that the resins have been stored, sometimes up to a year.

FIG. 4 shows the amount of Mu-IgG (ng) that was removed with the mock elution procedure performed at 2–8° C. There are four bars for each lot of resin, one bar representing each buffer that was assayed. When the columns were first packed, the buffer which was extracted during the packing was also submitted for Mu-IgG assay, this is the "column packing" bar seen on the graph. This buffer is expected to have high levels of Mu-IgG due to the length of time that the resin spent in this buffer. The Buffer A samples also have high levels of Mu-IgG since it is not possible to remove all of the "column packing" buffer (Buffer #1 with thimerosal) from the resin before starting the WIP procedure. The additive effect of the Buffer B plus mock elution washes was the removal of, on average, 20 ng/ml Mu-IgG or a total of 56 ng of Mu-IgG from the test resin columns. This is 1.4% of the amount of Mu-IgG removed by the 1M ethanolamine WIP at 2–8° C. (see FIG. 6). From these experiments, it was determined that wash-in-place with Buffer B and Buffer C washes was not effective in removing Mu-IgG from the MAb gel. The amount of Mu-IgG removed from each lot of resin was roughly the same. Therefore, this wash procedure would not be a useful way of determining the leaching potential of individual lots of resin.

Figure 5:
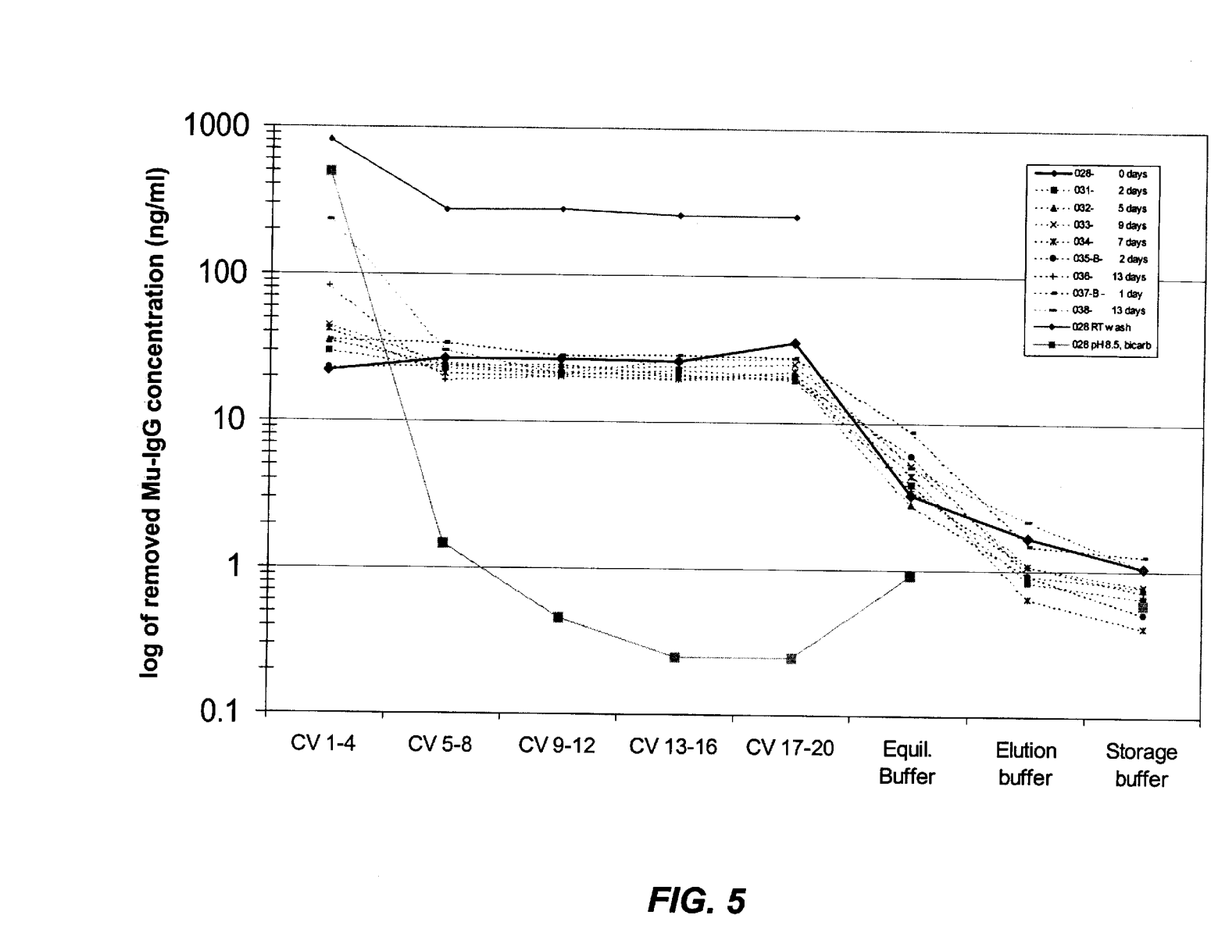

FIG. 5 shows the Mu-IgG levels for each of the buffer samples from the 1M buffered ethanolamine WIP from the nine lots. A control experiment to demonstrate the importance of buffer pH was done by washing a column of resin lot 028 with a buffer consisting of 0.2 M sodium bicarbonate at pH 8.5, without ethanolamine. For comparison, data are included from Example 1 in which a column packed with resin lot 028 was washed with 20 CV of 0.2M sodium bicarbonate with 1M ethanolamine, pH 8.5 at ambient temperature.

On the figure legend, the number of days indicates how long the resin sat in the column at 2–8° C. before being washed. This number affects the Mu-IgG concentration of the "CV1–4" samples since those resin lots that sat for a longer time (13 days) had high Mu-IgG concentrations in the first samples.

From these experiments, it was determined that the ethanolamine wash (WIP) done at 2–8° C. was not very effective, removing about ten-fold less Mu-IgG compared to washing (WIP) at ambient temperature (RT). Washing with buffered ethanolamine at 2–8° C. removed small, equivalent amounts of Mu-IgG which were contained in CV 5–20, and did not allow differences in leaching to be observed for individual resin lots. The pH test buffer (without ethanolamine) was also ineffective. Washing with 0.2M sodium bicarbonate, pH 8.5 removed about 100-fold less Mu-IgG than any of the 2–8° C. WIP washes using buffer with ethanolamine. Washing with cold MAb column buffers (Buffers A, B, and C) removed 10-fold less Mu-IgG than washing with cold, buffered ethanolamine.

Figure 6:
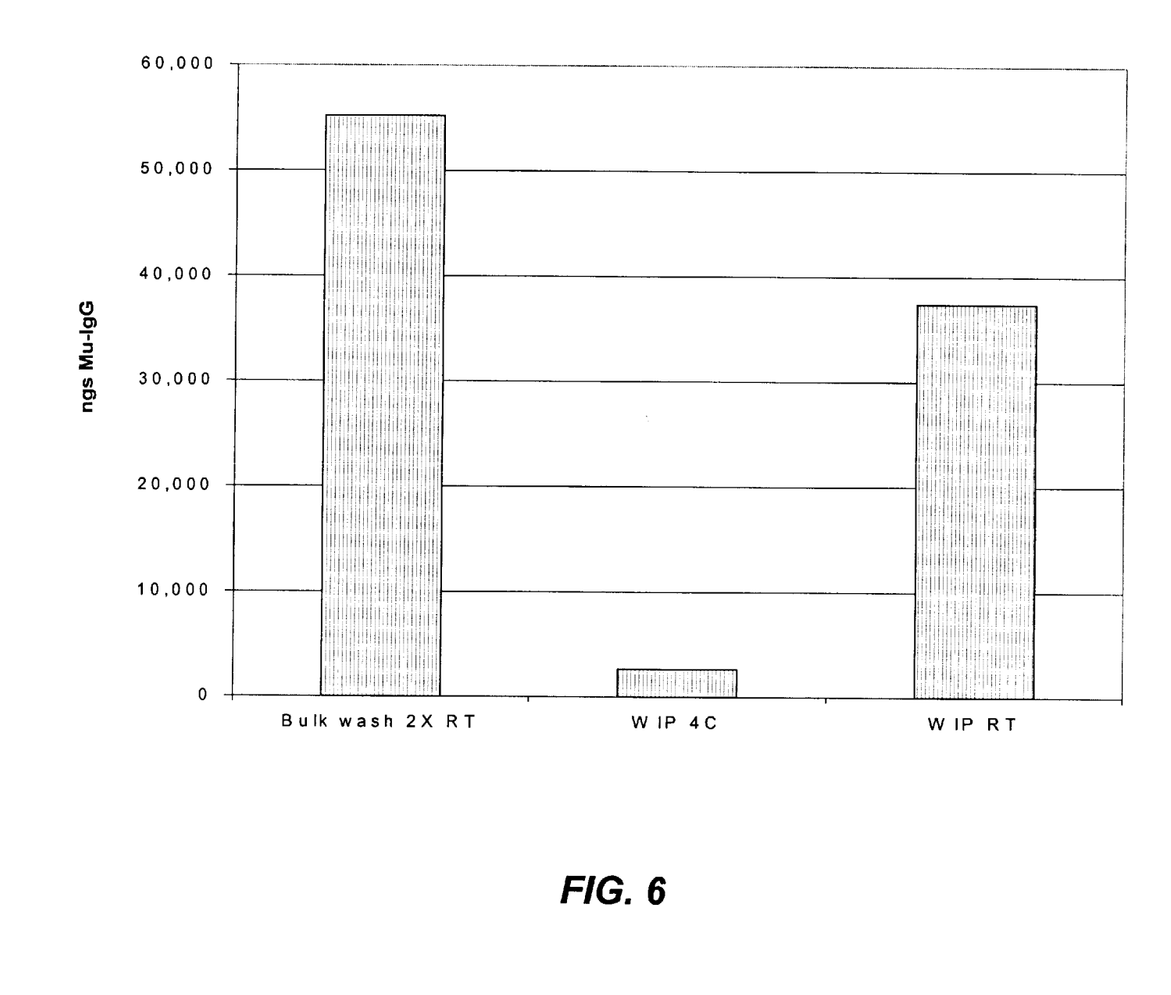
FIG. 6 shows a comparison of Mu-IgG removal by (a) a wash-in-place procedure at 2–8° C., (b) washing in place at ambient temperatures, and (c) washing in batch mode at ambient temperature. The bulk washing technique at ambient temperature is more effective than either wash-in-place method (2–8° C. or ambient temp).

In FIG. 6, the three different methods for removing Mu-IgG are compared. Resin lot 028 has been tested by all three methods. This figure shows the nanograms of Mu-IgG removed when the 028 resin lot was washed with: 1) 2×1 hour bulk washes with 1M buffered ethanolamine (BW-2X) at ambient temperature; 2) in a column format with 'wash-in-place' method with 20 CV of 1M buffered ethanolamine at 2–8° C. (WIP 4° C.); and 3) column format wash-in-place with 20 CV of 1 M buffered ethanolamine at ambient temperature (WIP RT). Neither the WIP 4° C. nor the WIP room temperature washing method was as efficient as the BW-2X at ambient temperature at removing Mu-IgG. The BW-2X method removed close to 55,000 ng whereas, the WIP RT removed approximately 37,000 ng and the WIP 4° C. method removed only around 4,000 ng.

5.0 CONCLUSIONS

The mock elution wash-in-place (WIP) procedure at 2–8° C., removed an average of 56 ng of Mu-IgG. For all nine lots of resin tested, the amount of Mu-IgG removed was about the same.

Washing at lower temperature (2–8° C.) reduced the efficiency of the ethanolamine wash compared to ambient wash protocols executed on the same scale with the same resin lots. Washing the test resin lots with 20 CV of buffered 1 M ethanolamine in the cold (2–8° C.) removed around 20 ng/ml of Mu-IgG for each CV of buffer. When lot 028 was washed with 20 CV at ambient temperature, the average concentration of Mu-IgG removed was 10-to-20 fold higher, 374 ng/ml per CV. Ambient WIP removed a total of 37 µg of Mu-IgG in 20 CV.

Each lot of resin had equivalent amounts of Mu-IgG removed by the 20 CV ethanolamine WIP at 2–8° C. Washing in place in the cold was inefficient. Very minor differences in the extent of leaching for individual lots of resin were determined.

When comparing the amount of Mu-IgG removed (in ng) by the three different 1M buffered ethanolamine washing methods: bulk washing at ambient temperature with 2 one-hour bulk washes was 30% more effective than WIP at ambient temperature. The ambient bulk washing method was 90% more effective than WIP at 2–8° C.

Example 3

Treatment of Nine Lots of Stored Anti-F8.1 MAb Immunoaffinity Resin with Buffered 1M Ethanolamine, pH 8.5

The bulk wash protocol described in Example 1 was employed in this Example to treat samples from nine lots of anti-FVIII (anti-F8. 1) MAb immunoaffinity resin that had been stored for varying lengths of time. Samples of these resins were treated with 1 M buffered ethanolamine, pH 8.5 following the "2×" 1-hour bulk wash protocol. This study demonstrates that it is possible to remove loosely bound Mu-IgG from previously coupled and stored immunoaffinity resin. Mu-IgG was quantitated using the IGEN immunoassay (see Example 1).

1. OVERVIEW

A bulk wash protocol with buffered ethanolamine was tested as a pre-commissioning wash for nine lots of anti-F8.1 MAb resin from storage in Buffer #1 containing 0.01% thimerosal. The purpose of the wash is to reduce the leachable concentrations of Mu-IgG, loosely bound, aggregated, or uncoupled antibody that could potentially co-elute from the MAb resin with rFVIII product during purification. The eight MAb resin lots were manufactured prior to the introduction of any improved washing protocol to the resin coupling process. The buffered ethanolamine wash protocol is described in detail in Example 1. Aliquots of eight anti-F8.1 MAb immunoaffinity resin lots were treated at small-scale with the recommended ambient temperature bulk wash process and buffered 1M ethanolamine solution.

2. METHODS AND MATERIALS

Samples from nine lots of MAb immunoaffinity resin from storage (Table 2.1) were treated with the "2×" i.e. two 1-hour bulk washes of buffered ethanolamine. MAb resin lot 028, a known high-leaching lot, was also washed and used as a control. Aliquots of resin were treated serially in two increments of one hour, using a fresh resin volume of 1M buffered ethanolamine, pH 8.5 each hour. Samples of the spent blocking buffer were stored briefly at 2–8° C. and tested for Mu-IgG concentrations.

TABLE 2

| # | RESIN LOT | AGE OF RESIN (months) |
|---|---|---|
| 1 | 028 | 23 |
| 2 | 031 | 16 |
| 3 | 032 | 13 |
| 4 | 033 | 11 |
| 5 | 034 | 11 |
| 6 | 035 | 6 |
| 7 | 036 | 6 |

TABLE 2-continued

| # | RESIN LOT | AGE OF RESIN (months) |
|---|---|---|
| 8 | 037 | 2 |
| 9 | 038 | 2 |

The Mu-IgG assay was performed as in Example 1. Spent buffer from the first and second washes of each lot of anti-F8.1 MAb resin were tested for Mu-IgG using this assay.

3. DISCUSSION AND CONCLUSIONS

The 1 M buffered ethanolamine washes were effective in removing Mu-IgG from each lot of resin. A comparison of the amount of Mu-IgG removed from the eight test lots with that removed from the control lot (028) could possibly be used as an indicator for high versus low leaching resin lots.

Figure 7:
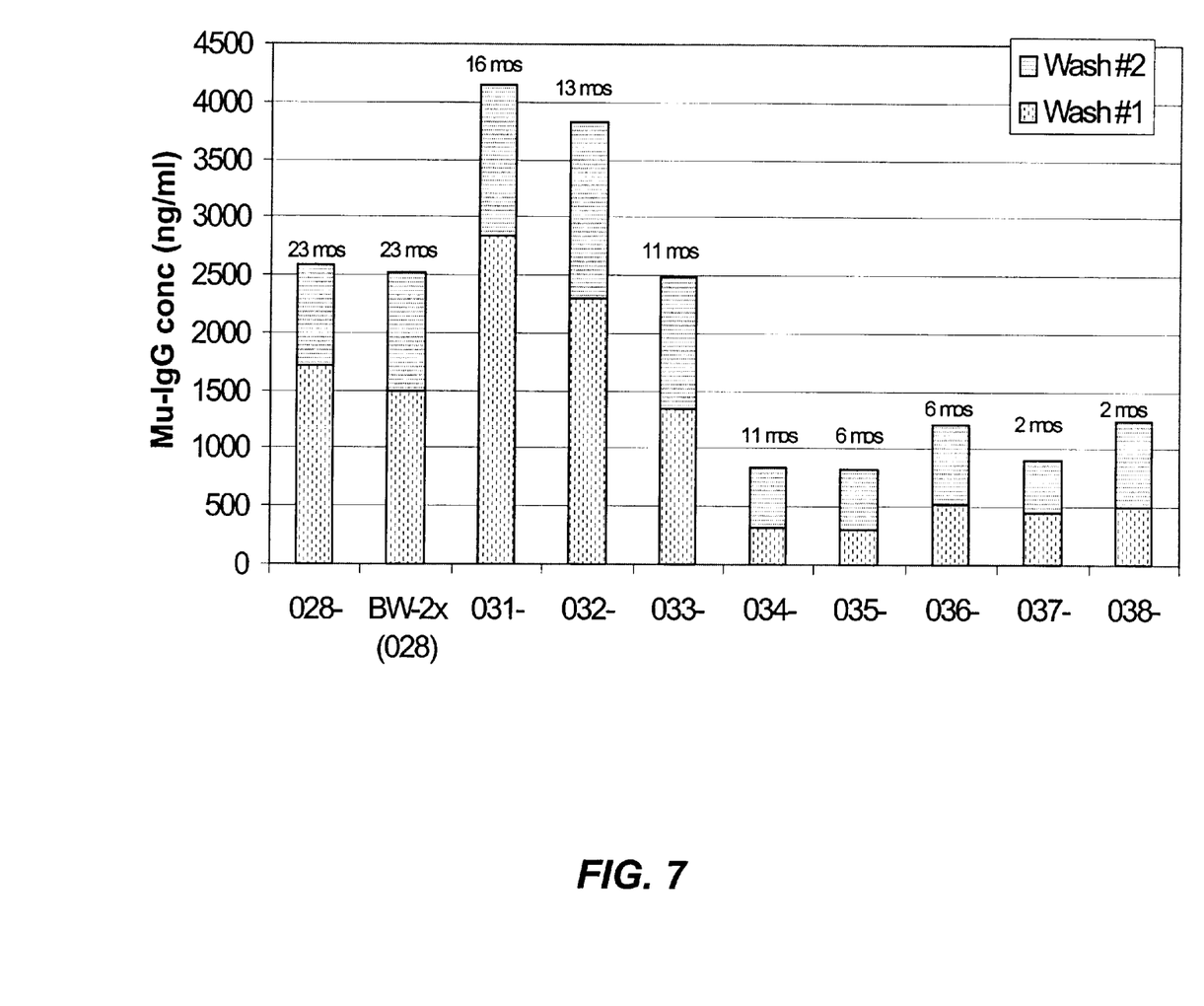
FIG. 7 shows the concentration of Mu-IgG removed from individual resin lots for each 1 M ethanolamine wash. The numbers over each bar represent the length of time each resin had been stored prior to performing the 2×1 hr bulk wash. Lot 028 was washed along with the other eight lots of resin as a control since it is a known high leaching lot. The bar labeled "BW-2X" is data taken from Example 1 which was also resin lot 028. When comparing both aliquots of resin 028, the 2×1 hr bulk washing procedure consistently removes the same concentration of Mu-IgG. Resin lots 031, 032 and 033 all had significantly more Mu-IgG removed than lots 034–038.

FIG. 7 shows the total concentration of Mu-IgG that was removed by the washes for all lots of MAb resin. In general, there was a decreasing trend in the amount of Mu-IgG that can be removed from the resin that correlates with decreasing age of the resin. The oldest resin that had been stored for the longest period of time, in general, had the highest amount of removable Mu-IgG. Resin prepared more recently had lower levels of Mu-IgG that could be removed by the ethanolamine wash. The results from this wash study provide evidence of loosely bound Mu-IgG in stored MAb resins, and they show the effectiveness of the wash method.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for decreasing leaching of a ligand from an affinity resin, the method comprising:
    (a) contacting an affinity resin with an effective amount of a hydroxyalkyl amine compound that comprises at least one hydroxyl moiety, wherein said affinity resin comprises a ligand conjugated to a chromatographic support and has been stored for at least 48 hours after coupling said ligand to said chromatographic support; and
    (b) incubating the affinity resin in the hydroxyalkyl amine compound for a time sufficient to remove unstably attached ligand from said affinity resin;
    wherein when said affinity resin is used to purify a molecule to which the ligand specifically binds, less ligand leaches from said affinity resin than when an aliquot of the affinity resin that has not been treated as described in (a) is used for the purification of the molecule.

2. The method of claim 1, wherein the method further comprises:
    (c) contacting the affinity resin with a second aliquot of an effective amount of the hydroxyalkyl amine compound and incubating the affinity resin in the hydroxyalkyl amine compound for a time sufficient to remove additional unstably attached ligand from said affinity resin.

3. The method of claim 1, wherein the chromatographic support is cyanogen bromide activated.

4. The method of claim 1, wherein sufficient unstably attached ligand is removed from the affinity resin so that after affinity purification the molecule is obtained in a solution which contains 300 ng of ligand per 100 μg of the molecule.

5. The method of claim 1, wherein said hydroxyalkyl amine compound comprises a straight chain alkyl amine.

6. The method of claim 1, wherein said hydroxyalkyl amine compound is ethanolamine.

7. The method of claim 1, wherein said hydroxyalkyl amine compound is present at a concentration between 500 mM and 1.5 M, inclusive.

8. The method of claim 7, wherein said hydroxyalkyl amine compound is present at a concentration between 750 mM and 1.2 M, inclusive.

9. The method of claim 8, wherein said hydroxyalkyl amine compound is present at a concentration between 0.9 and 1.1 M, inclusive.

10. The method of claim 6, wherein said hydroxyalkyl amine compound is present in a solution having a pH between 7 and 11.5, inclusive.

11. The method of claim 10, wherein said hydroxyalkyl amine compound is present in a solution having a pH between 8 and 9, inclusive.

12. The method of claim 11, wherein said hydroxyalkyl amine compound is present in a solution having a pH between 8.2 and 8.7, inclusive.

13. The method of claim 12, wherein said hydroxyalkyl amine compound is present at a concentration between 0.9 and 1.1 M, inclusive.

14. The method of claim 5, wherein said hydroxyalkyl amine compound is present in a solution that comprises tris(hydroxylmethyl)aminomethane.

15. The method of claim 1, wherein said method is performed after said resin has been stored for at least one week after coupling the ligand to the chromatographic support.

16. The method of claim 1, wherein said ligand is a polypeptide.

17. The method of claim 16, wherein said ligand is an antibody.

18. The method of claim 17, wherein said antibody specifically binds to Factor VIII.

19. The method of claim 1, herein said Factor VIII.

20. The method of claim 1, wherein said affinity resin has been stored in a solution that lacks an effective amount of a compound that comprises a $C_{1-4}$ alkyl amine and an alcohol moiety.

* * * * *